United States Patent [19]
Bahar

[11] Patent Number: 5,499,528
[45] Date of Patent: Mar. 19, 1996

[54] APPARATUS FOR MEASURING HOT GAS CONTENT

[75] Inventor: Bamdad Bahar, Baltimore, Md.

[73] Assignee: W. L. Gore & Associates, Inc., Newark, Del.

[21] Appl. No.: 312,259

[22] Filed: Sep. 26, 1994

[51] Int. Cl.$^6$ .............................. F16L 53/00; H05B 3/06; H05B 3/58
[52] U.S. Cl. .................. 73/23.2; 392/472; 392/480
[58] Field of Search .................. 73/23.2; 392/472, 392/480

[56] References Cited

U.S. PATENT DOCUMENTS

| | | | |
|---|---|---|---|
| 2,809,268 | 10/1957 | Heron | 219/46 |
| 3,522,413 | 8/1970 | Chrow | 219/301 |
| 3,727,029 | 4/1973 | Chrow | 219/301 |
| 3,965,748 | 6/1976 | Boubel et al. | 73/421.5 A |
| 4,038,519 | 7/1977 | Foucras | 219/301 |
| 4,910,086 | 3/1990 | Kawakami et al. | 428/419 |
| 4,976,135 | 12/1990 | Stock | 73/23.2 |
| 5,111,827 | 5/1992 | Rantala | 128/719 |
| 5,289,561 | 2/1994 | Costa Filho | 392/478 |
| 5,381,511 | 1/1995 | Bahar et al. | 392/472 |

*Primary Examiner*—Hezron E. Williams
*Assistant Examiner*—J. David Wiggins
*Attorney, Agent, or Firm*—Gary A. Samuels

[57] ABSTRACT

A gas monitoring apparatus with a heatable hose assembly having a central polymer tube of polyether ether ketone wrapped with a layer of polymer tape is described which is used to provide hot gases to a gas monitoring device. Heating elements for heating the central polymer tube can be arranged on the layer of polymer tape as can be an element for monitoring and controlling the element for heating the central polymer tube. Surrounding the arrangement can be a layer of thermal insulation and a protective jacket.

The assembly is of utility for use in systems for the monitoring of acid gases from emission stacks.

4 Claims, 2 Drawing Sheets

APPARATUS FOR MEASURING HOT GAS CONTENT

FIELD OF THE INVENTION

This invention relates to an apparatus for measuring hot gas content and to a tubular component used in such apparatus. More specifically, this invention relates to such an apparatus which employs a flexible hose capable of withstanding high temperatures.

BACKGROUND OF THE INVENTION

Heatable hoses or tubes have been used to transport hot gases to and from exit stacks without cooling the gas to below the dew point. Depending on the end-use requirements of these hoses, a variety of tubes have been used in the past to make the hoses. Commonly, the tube is made of a metal, such as stainless steel, providing the hose with a great deal of strength and chemical resistance. However, hoses having metal tubes, while readily available and reasonably inexpensive, are heavy and not very flexible.

Polymeric tubes are also known in the art. The polymeric tubes commonly used in heatable hoses are made of fluoro, polymers such as polytetrafluoroethylene (PTFE), copolymers of tetrafluoroethylene and perfluoro(propyl vinyl ether) (PFA) or fluorinated ethylene propylene copolymer (FEP). These fluoropolymers are fairly heat stable and exhibit a lower weight per unit length for a certain thickness tube than a comparable metal tube. Fluoropolymer tubes are also relatively flexible when compared to metal tubes of comparable sizes and shapes. However, hoses containing fluoropolymer tubes typically do not possess as much high strength as comparable hose containing a metal tube. This is of concern if the hose is of an extended length and is required to support its own weight. The strength of the fluoropolymer tube may be adversely effected by temperatures at which the hose may be heated. Also, fluoropolymer tubes exhibit a measure of permeation to certain gases, particularly acid gases such as $NO_x$ and $SO_x$. This is of concern when a hose containing a fluoropolymer tube is part of a gas sampling device attached to a emitting stack for the detection and measurement of acid gases.

It would be desirable to have a flexible heatable hose comprising a polymedic tube that is relatively light, relatively strong, relatively flexible and is relatively impermeable to many gases, even at elevated temperatures.

SUMMARY OF THE INVENTION

The invention is an apparatus for measuring content of stack gases comprising:
(a) a gas measuring device;
(b) a hose connected to said measuring device at one end and having an opposite end adapted to connect to a conduit for passing stack gases;
said hose comprising polyether ether ketone (PEEK).

The hose can be surrounded by a wrapped layer of heat-resistant polymer tape; or can be placed inside a fluoropolymer tube. Surrounding the polymer tube and wrapped layer of tape can be a layer of thermal insulation and then optionally an outside layer of protective jacket. Means for heating the hose can also be provided.

DETAILED DESCRIPTION OF THE INVENTION

Figure 1:
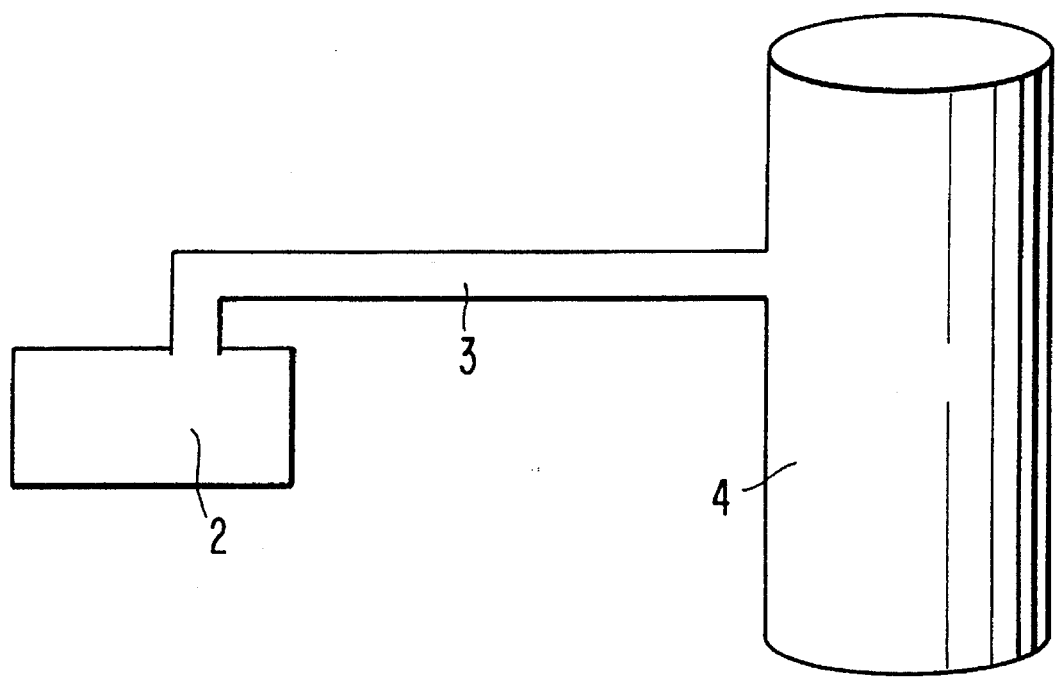
FIG. 1 shows the apparatus of the invention.

Referring to FIG. 1, the apparatus of the invention comprises a gas measuring device 2, tube 3, and a source of hot gases 4. In one embodiment, source 4 can be an exit stack for exiting hot gases from an enclosure. Tube 3 provides a conduit for transporting hot gases from stack 4 to gas measuring device 2. Device 2 can be any such device and is chosen depending on the gas desired to be monitored. For example, in the monitoring of gaseous emissions from industrial waste, commonly monitored are acid gases, such as $NO_x$ or $SO_x$. Thus the measuring device 2 can be selected to selectively monitor and record content of these gases in the mixture of hot emission gases.

Figure 2:
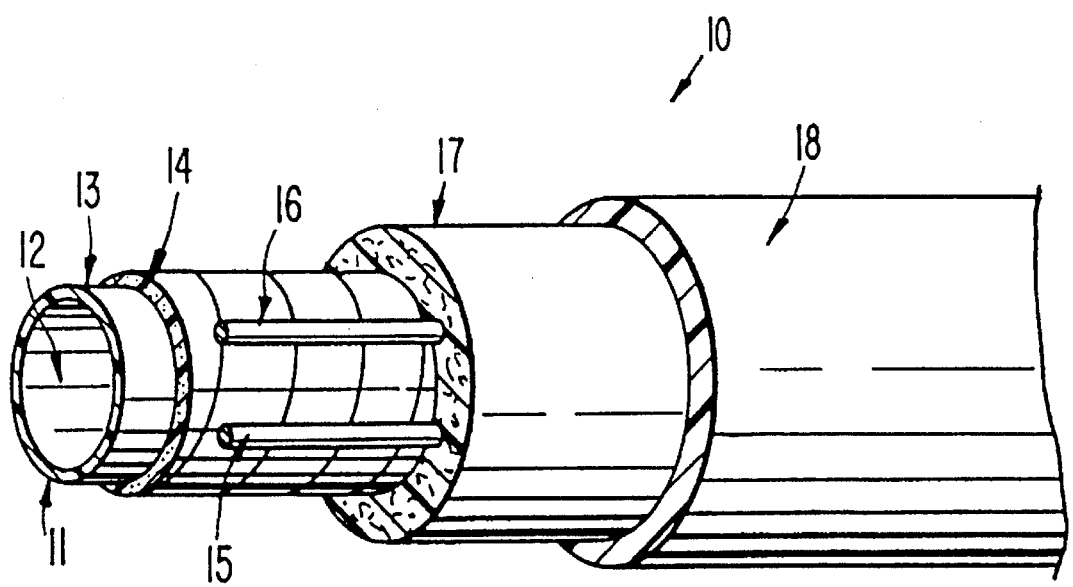
FIG. 2 is a perspective view, partly in cross-section, of a heatable hose used in the invention.
Figure 3:
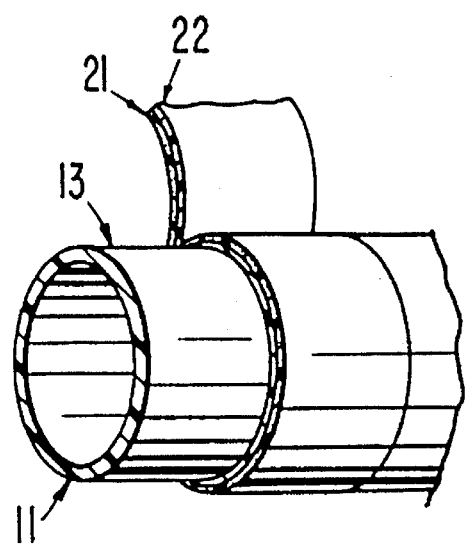
FIG. 3 is a perspective view, partly in cross-section, of a portion of the inventive heatable hose.

Referring now to FIG. 2, a cut-away section of hose 3 is shown with the various layers exposed. A central polymer tube 11 having a bore 12 and an outside surface 13 is depicted. The central polymeric tube 11 comprises polyether ether ketone (PEEK), and can be made by extrusion of melted PEEK polymer from an extruder through a rotating threaded die under vacuum while cooling the formed corrugated tube.

Upon the outside surface 13 of the central polymeric tube 11 is wrapped a layer of polymer tape 14. The tape may be of porous expanded polytetrafluoroethylene (ePTFE) made according to the method taught in U.S. Pat. No. 3,953,566 to W. L. Gore & Associates, Inc. The expanded porous tape may be compressed and densified to improve its strength.

In another embodiment tube 11 is placed inside a tube 14 of polytetrafluoroethylene or of stainless steel.

In addition, as shown in FIG. 2, the tape also may be a composite tape containing a layer of expanded PTFE 21 onto which is adhered a smooth layer of a thermoplastic polymer 22 having a melt point of 342° C. or less and a thickness of 50 micrometers or less)

The composite tape can be produced by:
(a) mixing PTFE resin with a hydrocarbon extrusion aid to form a paste;
(b) compressing the paste into a billet;
(c) extruding the billet through a die in a ram-type extruder to form a coherent PTFE shape;
(d) compressing the coherent PTFE shape;
(e) removing the hydrocarbon extrusion aid from the coherent PTFE shape;
(f) stretching the coherent PTFE shape 1.5 to 5 times its original length;
(g) contacting a surface of the coherent PTFE shape with a thermoplastic polymeric layer;
(h) heating the coherent PTFE shape to a temperature above the melt point of the thermoplastic polymeric layer and at or below 342° C.; and
(i) expanding the coherent PTFE shape at a temperature at or above the melt point of the thermoplastic polymeric layer and at or below 342° C.

The thermoplastic polymer may be polypropylene, polyamide, polyester, polyurethane, polyethylene or polyether ether ketone. Preferably, the thermoplastic polymer is a thermoplastic fluoropolymer. Thermoplastic fluoropolymers which are of utility as the thermoplastic polymer include fluorinated ethylene propylene (FEP), copolymer of tetrafluoroethylene and perfluoro(propylvinyl ether) (PFA), homopolymers of polychlorotrifluoroethylene (PTFE) and its copolymers with TFE or difluoroethylene (VF2), ethylene-chlorotrifluoroethylene (ECTFE) copolymer and its modifications, ethylene-tetrafluoroethylene (ETFE) copolymer and its modifications, polyvinylidene fluoride (PVDF), and polyvinylfluoride (PVF). Thermoplastic fluoropolymers are preferred as the thermoplastic polymer, since thermoplastic fluoropolymers are relatively high temperature resistant. Thermoplastic fluoropolymers are also relatively inert in nature and therefore exhibit resistance to degradation from many chemicals.

As shown in FIG. 2, the composite tape may be wrapped upon the outside surface of the central polymeric tube 11 so that the layer of ePTFE 21 is in contact with the outside surface of the central polymeric tube 11. Alternatively, the composite tape may be wrapped in such a manner that the smooth layer of thermoplastic polymer 22 is in contact with the outside surface of the central polymeric tube 11.

Wrapping of the tape on central polymeric tube 11 may be accomplished by hand. Preferably, wrapping of the tape on central polymeric tube 11 is accomplished through the use of a tape-wrap machine well known in the art of wrapping dielectric layers on conductors. The tape-wrap machine applies the tape with a degree of back tension in a helical fashion around the central polymeric tube.

Alternatively, the tape may be wrapped around the central polymeric tube in a longitudinal fashion so that the tape forms a longitudinal seam on the tube.

Referring back to FIG. 1, a heating means 16 for heating the central polymeric tube and a monitoring means 15 for monitoring and controlling the heating of the central polymeric tube are placed longitudinally on the layer of tape. The means for heating the central polymeric tube is commonly an electrical heating wire or resistor, including resistors containing carbon, having a certain electrical resistance such that when an electrical current flows through the wire, a measure of energy present in the electrical current is lost in the form of heat. The means 15 for monitoring and controlling means 16 for heating the central polymeric tube is commonly a thermocouple wire.

Surrounding the arrangement of the means 16 for heating the central polymeric tube 13 and means 15 for monitoring and controlling the means for heating the central polymeric tube is a layer of thermal insulation 17, which can be any heat resistant insulation, such as glass fiber or Nomex/aromatic polyamide, or the like. Surrounding the layer of thermal insulation 17 is a jacket 18. Jacket 18 provides physical protection to the heated hose. Jacket 18 may be in the form of a polymeric material extruded or tape wrapped upon the layer of thermal insulation 17. Representative materials for the jacket include polyvinyl chloride, FEP, PFA, PTFE, ePTFE, nitrile rubber, butyl rubber, urethane or the like. Jacket 18 can be in the form of a metal braid.

In one embodiment, a helically convoluted PEEK central polymeric tube was used having a relative density of 1.4 g/cm. The tape 14 contained ePTFE having a coating of FEP on it. The conductive wire for heating was a nickel/chromium wire. The means for monitoring and controlling was a thermocouple wire. The thermal insulation 17 was glass fiber and the jacket 18 made of polyvinyl chloride.

In another embodiment, a PEEK tube ⅜ inch diameter with a 40 mil wall thickness was wrapped with insulation and in open weave wire braiding.

Other embodiments of the invention will be apparent to those skilled in the art from a consideration of this specification or practice of the invention disclosed herein. It is intended that the specification be considered as exemplary only, with the true scope and spirit of the invention being indicated by the following claims.

We claim:

1. An apparatus for measuring content of stack gases comprising:

(a) a gas measuring device;

(b) a hose connected to said measuring device at one end and having an opposite end adapted to connect to a conduit for passing stack gases;

said hose comprising;

(I) a central polymer tube comprising polyether ether ketone;

(ii) a layer of polymer tape wrapped upon the outside surface of said central polymer tube;

(iii) means for heating said central polymer tube and a means for monitoring and controlling the means for heating the central polymer tube such that the means for heating, along with said means for monitoring and controlling is arranged on the layer of polymer tape and extends along the length of said central polymer tube;

(iv) a layer of thermal insulation surrounding the means for heating, along with said means for monitoring and controlling said heating means, applied onto said polymer tape; and (v) a protective jacket surrounding said thermal insulation layer.

2. The apparatus of claim 1 wherein the polymer tape (ii) comprises expanded porous polytetrafluoroethylene.

3. The apparatus of claim 1, wherein the polymer tape (ii) comprises expanded porous polytetrafluoroethylene having a layer of a thermoplastic fluoropolymer on said expanded, porous polytetrafluoroethylene.

4. A hose for use in an apparatus for measuring content of stack gases which comprises a tube of polyether ether ketone located inside an, adjacent concentric tube made of a material selected from the class consisting of polytetrafluoroethylene and steel.

\* \* \* \* \*